United States Patent
Lee et al.

(10) Patent No.: US 10,465,008 B2
(45) Date of Patent: Nov. 5, 2019

(54) ANTIBODIES AGAINST VASCULAR ENDOTHELIAL GROWTH FACTOR RECEPTOR 2 (VEGFR2), ENCODING NUCLEIC ACID MOLECULES AND METHODS FOR TREATING AN ANGIOGENESIS-RELATED DISEASE

(71) Applicant: ABCLON INC., Seoul (KR)

(72) Inventors: Jong Seo Lee, Gyeonggi-do (KR); Kyu Tae Kim, Gyeonggi-do (KR); Bong Kook Ko, Seoul (KR); Ki Hyun Kim, Seoul (KR); Hyun Jong Lee, Incheon (KR)

(73) Assignee: ABCLON INC., Seoul (KR)

( * ) Notice: Subject to any disclaimer, the term of this patent is extended or adjusted under 35 U.S.C. 154(b) by 0 days.

(21) Appl. No.: 15/780,046

(22) PCT Filed: Nov. 25, 2016

(86) PCT No.: PCT/KR2016/013735
§ 371 (c)(1),
(2) Date: May 30, 2018

(87) PCT Pub. No.: WO2017/095088
PCT Pub. Date: Jun. 8, 2017

(65) Prior Publication Data
US 2019/0241666 A1    Aug. 8, 2019

(30) Foreign Application Priority Data
Nov. 30, 2015    (KR) .................. 10-2015-0168859

(51) Int. Cl.
C07K 16/28    (2006.01)
G01N 33/577    (2006.01)
A61P 37/06    (2006.01)
A61P 35/00    (2006.01)

(52) U.S. Cl.
CPC .......... C07K 16/2863 (2013.01); A61P 35/00 (2018.01); A61P 37/06 (2018.01); G01N 33/577 (2013.01)

(58) Field of Classification Search
CPC ... C07K 16/2863; G01N 33/577; A61P 35/00; A61P 37/06
See application file for complete search history.

(56) References Cited

U.S. PATENT DOCUMENTS

| 7,947,809 B2 | 5/2011 | Yan et al. |
| 2011/0038874 A1 | 2/2011 | Tong et al. |
| 2014/0294827 A1 | 10/2014 | Gastwirt et al. |

FOREIGN PATENT DOCUMENTS

| CN | 103965356 A | 8/2016 |
| JP | 2015-533126 A | 11/2015 |
| WO | 2013/067098 A1 | 5/2013 |
| WO | 2014/055998 A1 | 4/2014 |

OTHER PUBLICATIONS

Extended European Search Report dated Nov. 30, 2018, including the Supplementary European Search Report and the European Search Opinion, in connection with corresponding EP Application No. 16870984.8 (6 pgs.).
Yelena Krupitskaya, et al., "Ramucirumab, a fully human mAb to the transmembrane signaling tyrosine kinase VEGFR-2 for the potential treatment of cancer", Current Opinion in Investigational Drugs, Thomson Reuters, vol. 10, No. 6, Jun. 1, 2009, pp. 597-605 (9 pgs. total).
International Search Report dated Mar. 16, 2017 and Response to the Written Opinion of corresponding International application No. PCT/KR2016/013735; 8 pgs.
Xuan et al., "Fully human VEGFR2 Monoclonal Antibody BC0OJ Attenuates Tumor Angiogenesis and inhibits Tumor Growth", International Journal of Oncology, vol. 45, pp. 2411-2420 (2014), 10 pgs.
Aprile et al. Drugs. 73(18); 2003-2015 (2013), 10 pgs.
Chan et al. Biologics. 22(9):93-105 (2015), 13 pgs.
Spratlin et al. J Clon Oncol. 28(5):780-787 (2010), 8 pgs.
Spratlin et al. Future Oncol. 6(7):1085-1094 (2010), 10 pgs.
Ellis and Hicklin. Nat Rev Cancer. 8(8):579-591 (2008), 13 pgs.
Youssoufian et al. Clin Cancer Res. 13(18Pt2):5544s-5548s. (2007), 6 pgs.
Risau. Nature.386(6626):671-674 (1997), 4 pgs.
Carmeliet and Jain. Nature. 407(4801):249-257 (2000), 9 pgs.

*Primary Examiner* — Robert S Landsman
(74) *Attorney, Agent, or Firm* — Maier & Maier, PLLC

(57) ABSTRACT

A novel antibody against VEGFR2 for use in the prevention or treatment of macular degeneration and cancer, which are angiogenesis-related diseases. The antibody of the present invention is an antibody which specifically binds to VEGFR2 which is overexpressed in vascular endothelial cells. The antibody of the present invention has very low homology compared to the CDR sequences of conventional VEGFR2 target antibodies, and thus is unique in its sequence. Since the antibody of the present invention, when treated alone, has the ability to inhibit vascular endothelial cell growth equivalent to that of ramucirumab which is conventionally used, it is very effective to prevent or treat angiogenesis-related diseases.

19 Claims, 8 Drawing Sheets

Specification includes a Sequence Listing.

ANTIBODIES AGAINST VASCULAR ENDOTHELIAL GROWTH FACTOR RECEPTOR 2 (VEGFR2), ENCODING NUCLEIC ACID MOLECULES AND METHODS FOR TREATING AN ANGIOGENESIS-RELATED DISEASE

TECHNICAL FIELD

The present invention was made with the support of the Ministry of Trade, Industry and Energy, Republic of Korea, under Project No. 1415118385, which was conducted under the research project entitled "International Joint Technology Development Project" within the project named "Innovative Epitope Development Platform Technology-Based Global Antibody Drug Development" by AbClon Inc. under the management of the Korea Evaluation Institute of Industrial Technology, from 1 Nov. 2011 to 31 Oct. 2014.

This application claims priority to and the benefit of Korean Patent Application No. 10-2015-0168859 filed in the Korean Intellectual Property Office on 30 Nov. 2015, the disclosure of which is incorporated herein by reference.

The present invention relates to a vascular endothelial growth factor receptor 2 (VEGFR2) antibody used for the prevention or treatment of a human VEGFR2-related disease, especially, an angiogenesis-related disease.

BACKGROUND ART

Angiogenesis is a mechanism in which new blood vessels are generated from existing blood vessels by growth, division, migration, and the like, of endothelial cells. The angiogenesis plays an important role in the normal growth process including wound healing or female menstrual cycles. However, abnormal angiogenesis is known to play a crucial role in diseases, such as macular degeneration (MD), diabetic retinopathy, cancer growth and metastasis, psoriasis, rheumatoid arthritis, and chronic inflammation (Risau. *Nature*. 386(6626):671-674 (1997), and Carmeliet and Jain. *Nature*. 407(4801):249-257 (2000)).

A vascular endothelial growth factor (VEGF) is a representative angiogenesis inducing factor. VEGF is an important factor that regulates not only adult angiogenesis but also vasculogenesis in the embryonic development. Five types of VEGF (VEGF-A, VEGF-B, VEGF-C, VEGF-D, and PLGF) have been revealed to this date, and these are known to bind to VEGF receptors (VEGFRs) 1, 2 and 3, and co-receptors, such as heparin sulphate proteoglycans (HSPGs) and neuropilins (NRPB).

It is known that VEGF binds to VEGFR1 and VEGFR2, among several types of receptors, with very high affinity, and induces an angiogenic mechanism, such as proliferation and migration of vascular endothelial cells, mainly through VEGFR2. Therefore, VEGF and VEGFR2 have been major targets for inhibiting angiogenesis-related diseases (Ellis and Hicklin. *Nat Rev Cancer*. 8(8):579-591 (2008); Youssoufian et al. *Clin Cancer Res*. 13(18Pt2):5544s-5548s. (2007)).

Ramucirumab, which is an antibody that has been used and approved among antibodies targeting VEGFR2, is commercialized as CYRAMZA, and many studies thereof have been conducted. Ramucirumab, which is a monoclonal antibody selected from the full human Fab library, has been approved for use in colon cancer, non-small cell lung cancer, and stomach cancer (Spratlin et al. *J Clon Oncol*. 28(5): 780-787 (2010); Spratlin et al. *Future Oncol*. 6(7):1085-1094 (2010); Aprile et al. *Drugs*. 73(18); 2003-2015 (2013); and Chan et al. *Biologics*. 22(9):93-105 (2015)).

Throughout the specification, many papers and patent documents are used as references, and the citations thereof are represented. The disclosure of the cited papers and patent documents is incorporated in the present specification by reference in its entirety, to describe a level of a technical field to which the present invention pertains and content of the present invention more clearly.

DETAILED DESCRIPTION OF THE INVENTION

Technical Problem

The present inventors have endeavored to develop an antibody showing higher or equivalent activity compared with ramucirumab, which is an anticancer drug targeting VEGFR2 to inhibit angiogenesis. As a result, the present inventors confirmed that the antibody of the present invention exhibits excellent binding ability to VEGFR2, has inhibitory ability to endothelial cell growth equal to that of ramucirumab, and has inhibitory ability to angiogenesis and endothelial cell invasion, and thus completed the present invention.

An aspect of the present invention is to provide an antibody against VEGFR2 or an antigen binding fragment thereof.

Another aspect of the present invention is to provide a nucleic acid molecule encoding an antibody against VEGFR2 or an antigen binding fragment thereof.

Still another aspect of the present invention is to provide a recombinant vector including the nucleic acid molecule.

Still another aspect of the present invention is to provide a host cell transformed with the recombinant vector.

Still another aspect of the present invention is to provide a pharmaceutical composition for preventing or treating an angiogenesis-related disease, the pharmaceutical composition containing an antibody against vegfr2 or an antigen binding fragment thereof.

Still another aspect of the present invention is to provide a kit for diagnosis of an angiogenesis-related disease and analysis of drug responsiveness, the kit containing an antibody against vegfr2 or an antigen binding fragment thereof.

Still another aspect of the present invention is to provide a method for preventing or treating an angiogenesis-related disease, the method including a step for administering, to a subject, a pharmaceutical composition containing an antibody against vegfr2 or an antigen binding fragment thereof as an active ingredient.

Other purposes and advantages of the present disclosure will become more obvious with the following detailed description of the invention, claims, and drawings.

Technical Solution

In accordance with an aspect of the present invention, there is provided an antibody against vascular endothelial growth factor receptor 2 (VEGFR2) or an antigen binding fragment thereof, the antibody including:

(a) a heavy chain variable region including the following heavy chain complementarity determining region (CDR) amino acid sequences: CDRH1 of SEQ ID NO: 1, CDRH2 of SEQ ID NO: 2, and CDRH3 of SEQ ID NO: 3; and (b) a light chain variable region having the following light chain CDR amino acid sequences: CDRL1 of SEQ ID NO: 4, CDRL2 of SEQ ID NO:5, and CDRL3 of SEQ ID NO: 6.

The present inventors have endeavored to develop an antibody showing higher or equivalent activity compared with ramucirumab, which is an anticancer drug targeting VEGFR2 to inhibit angiogenesis. As a result, the present inventors confirmed that the antibody of the present invention exhibits excellent binding ability to VEGFR2, has inhibitory ability to endothelial cell growth equal to that of ramucirumab, and has inhibitory ability to angiogenesis and endothelial cell invasion.

As used herein, the term "ramucirumab" refers to an antibody disclosed in U.S. Pat. No. 7,498,414 B2.

The antibody of the present invention has excellent killing ability or proliferation inhibitory ability on VEGFR2-expressing cells. As used herein, the terms "killing" and "proliferation inhibiting" used citing an angiogenesis-related disease inhibitory effect are used interchangeably.

As used herein, the term "antibody" comprises not only the whole antibody form but also an antigen binding fragment of the antibody molecule.

The whole antibody has a structure having two full-length light chains and two full-length heavy chains, and the light chains are linked with the heavy chains via disulfide bonds, respectively. Each heavy chain constant region has gamma (γ), mu (μ), alpha (α), delta (δ), and epsilon (ε) types, and gamma1 (γ1), gamma2 (γ2), gamma3 (γ3), gamma4 (γ4), alpha1 (α1), and alpha2 (α2) subclasses. Each light chain constant region has kappa (κ) and lambda (λ) types (Cellular and Molecular Immunology, Wonsiewicz, M. J., Ed., Chapter 45, pp. 41-50, W. B. Saunders Co. Philadelphia, Pa. (1991); Nisonoff, A., Introduction to Molecular Immunology, 2nd Ed., Chapter 4, pp. 45-65, sinauer Associates, Inc., Sunderland, Mass. (1984)).

As used herein, the term "antigen binding fragment" refers to a fragment that retains an antigen binding function, and comprises Fab, F(ab'), F(ab')2, and Fv. Out of the antibody fragments, Fab has a structure of having heavy chain and light chain variable regions, a light chain constant region, and a first heavy chain constant region ($C_{H1}$), and Fab has one antigen binding site. Fab' is different from Fab in that Fab' has a hinge region including one or more cysteine residues at the C-terminus of the heavy chain $C_{H1}$ domain. F(ab')$_2$ antibody is generated through a disulfide bond formed between the cysteine residues in the hinge regions of Fab' fragments. Fv is a minimal antibody segment having only a heavy chain variable domain and a light chain variable domain, and a recombinant technique that produces an Fv fragment is disclosed in WO 88/10649, WO 88/106630, WO 88/07085, WO 88/07086, and WO 88/09344. A two-chain Fv has a structure in which a heavy chain variable region and a light chain variable region are linked through a non-covalent linkage, and a single-chain Fv comprises a heavy chain variable region and a light chain variable region covalently linked to each other via a peptide linker or directly linked at the C-terminus, thereby forming a dimeric structure as in the two-chain Fv. These antibody fragments may be obtained using proteases (for example, the whole antibody is restriction digested with papain to obtain Fab fragments, and is restriction digested with pepsin to obtain F(ab')$_2$ fragments), and may be fabricated by a genetic recombinant technique.

The antibody of the present invention is a form of Fab or the whole antibody. In addition, the heavy chain constant region may be selected from any one isotype of gamma (γ), mu (μ), alpha (α), delta (δ), and epsilon (ε) types. According to an embodiment, the constant region comprises gamma1 (IgG1), gamma3 (IgG3), and gamma4 (IgG4) isotypes, and according to another embodiment, the constant region is gamma1 (IgG1) isotype. The light chain constant region may be κ or λ isotype, and according to an embodiment, the light chain constant region is κ isotype. Therefore, according to an embodiment of the present invention, the antibody of the present invention is in a Fab or IgG1 type having a kappa (κ) light chain and a gamma1 (γ1) heavy chain.

As used herein, the term "heavy chain" refers to the full-length heavy chain and fragments thereof, the full-length heavy chain including a variable region domain $V_H$ that comprises an amino acid sequence sufficient to provide specificity to an antigen, and three constant region domains, $C_{H1}$, $C_{H2}$, and $C_{H3}$. In addition, as used herein, the term "light chain" refers to the full-length light chain and fragments thereof, the full-length light chain including a variable domain VL that comprises an amino acid sequence sufficient to impart specificity to an antigen, and a constant domain CL.

As used herein, the term "complementarity determining region (CDR)" refers to an amino acid sequence of a hypervariable region of an immunoglobulin heavy chain or light chain (Kabat et al., *Sequences of Proteins of Immunological Interest*, 4th Ed., U.S. Department of Health and Human Services, National Institutes of Health (1987)). The heavy chain and light chain include three CDRs (heavy chain CDRH1, CDRH2, and CDRH3) and light chain CDRL1, CDRL2, and CDRL3), respectively. CDRs provide major contact residues in the binding of an antibody to an antigen or epitope.

The Antibody against VEGFR2 or antigen binding fragment thereof of the present invention may contain variants of the amino acid sequences described in the attached sequence listing within a range that can specifically recognize VEGFR2. For example, the amino acid sequence of the antibody may be varied to improve the binding affinity and/or other biological characteristics of the antibody. Such variation comprises, for example, deletion, insertion, and/or substitution of amino acid residues of the antibody.

Such amino acid variation is made on the basis of relative similarity, for example, hydrophobicity, hydrophilicity, charge, size, or the like, of amino acid side chain substituents. It can be seen from the analysis of size, shape, and type of the amino acid side chain substitutions that: all of arginine, lysine, and histidine are positively charged residues; alanine, glycine, and serine have similar sizes; and phenylalanine, tryptophan, and tyrosine have similar shapes. Therefore, on the basis of these considerations, arginine, lysine, and histidine; alanine, glycine, and serine; and phenylalanine, tryptophan, and tyrosine may be considered to be biologically functional equivalents.

For introducing such variation, hydropathic indexes of amino acids may be considered. Each amino acid has been assigned a hydropathic index on the basis of hydrophobicity and charge characteristics thereof: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5)

The hydrophobic amino acid indexes are very important in giving interactive biological functions of proteins. It is well known that amino acids with similar hydrophobic indexes need to be substituted with each other to retain similar biological activities. In cases where a variation is introduced with reference to the hydrophobic indexes, the substitution is made between amino acids having a difference in the hydrophobic index within preferably ±2, more preferably ±1, and still more preferably ±0.5.

Meanwhile, it is also well known that the substitution between amino acids with similar hydrophilicity values results in proteins having equivalent biological activity. As disclosed in U.S. Pat. No. 4,554,101, each amino acid residue has been assigned the following hydrophilicity values: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4)

In cases where the variation is introduced with reference to the hydrophilic indexes, the substitution is made between amino acids having a hydrophilicity value difference within preferably ±2, more preferably ±1, and still more preferably ±0.5.

The amino acid change in proteins, which does not substantially alter molecular activity, is known in the art (H. Neurath, R. L. Hill, The Proteins, Academic Press, New York, 1979). The most common occurring exchanges are exchanges between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

Considering the foregoing variations having biological equivalent activity, the antibody or the nucleic acid molecule encoding the antibody of the present invention is construed to also include sequences having substantial identity to the sequences described in the sequence listings. The substantial identity means that, when the sequence of the present invention and another optional sequence are aligned to correspond to each other as much as possible and the aligned sequences are analyzed using an algorithm that is commonly used in the art, the corresponding sequences have at least 61%, more preferably at least 70%, still more preferably at least 80%, and most preferably at least 90% sequence identity. Methods of alignment for sequence comparison are known in the art. Various methods and algorithms for alignment are disclosed in Smith and Waterman, *Adv. Appl. Math.* 2:482(1981); Needleman and Wunsch, *J. Mol. Bio.* 48:443(1970); Pearson and Lipman, *Methods in Mol. Biol.* 24: 307-31(1988); Higgins and Sharp, *Gene* 73:237-44 (1988); Higgins and Sharp, *CABIOS* 5:151-3(1989); Corpet et al., *Nuc. Acids Res.* 16:10881-90(1988); Huang et al., *Comp. Appl. BioSci.* 8:155-65(1992); and Pearson et al., *Meth. Mol. Biol.* 24:307-31(1994). The NCBI Basic Local Alignment Search Tool (BLAST) (Altschul et al., *J. Mol. Biol.* 215:403-10(1990)) is available from several sources, including the National Center for Biological Information (NCBI), and on the Internet, for use in connection with the sequence analysis programs blastp, blasm, blastx, tblastn, and tblastx. BLAST can be accessed at the BLAST webpage from the website of the National Center for Biotechnology Information from the U.S. National Library of Medicine of the U.S. National Institute of Health. The sequence identity comparison method using such a program can be confirmed in from the BLAST webpage of the web site of the National Center for Biotechnology Information from the U.S. National Library of Medicine of the U.S. National Institute of Health.

According to an embodiment of the present invention, the heavy chain variable region of the present invention comprises the amino acid sequence of SEQ ID NO: 8.

According to an embodiment of the present invention, the light chain variable region of the present invention comprises the amino acid sequence of SEQ ID NO: 10.

The antibody of the present invention comprises monoclonal antibodies, multi-specific antibodies, human antibodies, humanized antibodies, chimeric antibodies, single chain Fvs (scFVs), single chain antibodies, Fab fragments, F(ab') fragments, disulfide-linked Fvs (sdFVs), and anti-idiotype (anti-Id) antibodies, and epitope-binding fragments of the antibodies, but is not limited thereto.

Meanwhile, the antibody CDR sequences of the present invention have very low similarity when compared with the CDR sequences of conventional antibodies, and thus has distinctive sequences. For example, when compared with the antibodies of the present invention, the protein disclosed in U.S. Pat. No. 7,947,809, which has been found to have the highest homology in the BLAST search (from the BLAST webpage of the website of the National Center for Biotechnology Information from the U.S. National Library of Medicine of the U.S. National Institute of Health), has aCDRH3 sequence homology of 71%, little CDRL3 sequence homology, and a total CDR sequence homology of less than 50%. Moreover, the antibody described in U.S. Pat. No. 7,947,809 is an antibody recognizing glucagon receptors, and the targets thereof are different from those of the antibodies of the present invention.

In accordance with another aspect of the present invention, there is provided a nucleic acid molecule encoding a heavy chain variable region of an antibody against VEGFR2, the heavy chain variable region comprising the amino acid sequence of SEQ ID NO: 8.

According to an embodiment of the present invention, the nucleic acid molecule comprises the nucleotide sequence of SEQ ID NO: 7.

In accordance with still another aspect of the present invention, there is provided a nucleic acid molecule encoding a light chain variable region of an antibody against VEGFR2, the light chain variable region comprising the amino acid sequence of SEQ ID NO: 10.

According to an embodiment of the present invention, the nucleic acid molecule comprises the nucleotide sequence of SEQ ID NO: 9.

As used herein, the term "nucleic acid molecule" refers to comprehensively including DNA (gDNA and cDNA) and RNA molecules, and the nucleotide as a basic constituent unit in the nucleic acid molecule comprises natural occurring nucleotides, and analogues with modified sugars or bases (Scheit, *Nucleotide Analogs*, John Wiley, New York (1980); Uhlman, and Peyman, *Chemical Reviews*, 90:543-584(1990)). The nucleic acid molecule sequences encoding the heavy chain variable region and the light chain variable region of the present invention may be modified. Such a modification comprises addition, deletion, or non-conservative substitution or conservative substitution.

The nucleic acid molecule encoding antibodies against VEGFR2 in the present invention is construed to also include a nucleotide sequence showing substantial identity to the foregoing nucleotide sequence. The substantial identity means that, when the present nucleotide sequence and any difference sequence are aligned to correspond to each other as much as possible and the aligned sequences are analyzed using an algorithm that is ordinarily used in the art, the nucleotide sequences show at least 80% homology, preferably at least 90% homology, and most preferably at least 95% homology.

In accordance with still another aspect of the present invention, there is provided a recombinant vector comprising the foregoing nucleic acid molecule.

As used herein, the term "vector" refers to any vehicle that is used to express a target gene in a host cell, and encompasses: plasmid vectors; cosmid vectors; and viral vectors, such as bacteriophage vectors, adenoviral vectors, retroviral vectors, and adeno-associated viral vectors.

According to an embodiment, the nucleic acid molecule encoding a light chain variable region and the nucleic acid molecule encoding a heavy chain variable region are operatively linked with a promoter.

As used herein, the term "operatively linked" refers to a functional linkage between a nucleic acid expression control sequence (e.g., a promoter, a signal sequence, or an array of transcription regulation factor binding sites) and another nucleic acid sequence, and through the linkage, the control sequence controls the transcription and/or translation of the another nucleic acid sequence.

The recombinant vector system of the present invention can be constructed by various methods known in the art, and a specific method thereof is disclosed in Sambrook et al., *Molecular Cloning, A Laboratory Manual*, Cold Spring Harbor Laboratory Press(2001), which is incorporated herein by reference.

The vector of the present invention may be typically constructed as a vector for cloning or a vector for expression. In addition, the vector of the present invention may be constructed by using a prokaryotic or eukaryotic cell as a host.

For example, in cases where the vector of the present invention is an expression vector and employs a eukaryotic cell as a host cell, a promoter derived from the genome of mammalian cells (e.g.: metallothionein promoter, β-actin promoter, human hemoglobin promoter, and human muscle creatine promoter) or a promoter derived from mammalian viruses (e.g.: adenovirus late promoter, vaccinia virus 7.5K promoter, SV40 promoter, cytomegalovirus promoter, tk promoter of HSV, mouse mammary tumor virus (MMTV) promoter, LTR promoter of HIV, promoter of Moloney virus, Epstein-Barr virus (EBV), and Rous sarcoma virus (RSV)) may be used, and a polyadenylated sequence may be commonly used as the transcription termination sequence.

The vector of the present invention may be fused with the other sequences to facilitate the purification of the antibody expressed therefrom. Examples of the fusion sequence include, for example, glutathione S-transferase (Pharmacia, USA), maltose binding protein (NEB, USA), FLAG (IBI, USA), and 6× His (hexa-histidine; Quiagen, USA).

In addition, since the protein expressed by the vector of the present invention is an antibody, the expressed antibodies can be easily purified through a protein A column or the like even without additional sequences for purification.

Meanwhile, the expression vector of the present invention comprises, as a selective marker, an antibiotic agent-resistant gene that is ordinarily used in the art and may include resistant genes against ampicillin, gentamycin, carbenicillin, chloramphenicol, streptomycin, kanamycin, geneticin, neomycin, and tetracycline.

In accordance with still another aspect of the present invention, there is provided a host cell transformed with the recombinant vector.

The host cells capable of stably and continuously cloning and expressing the vector of the present invention may be any host cell that is known in the art, and for example, suitable eukaryotic host cells for the vector may be monkey kidney cells 7 (COS7), NSO cells, SP2/0, Chinese hamster ovary (CHO) cells, W138, baby hamster kidney (BHK) cells, MDCK, myeloma cell lines, HuT 78 cells, and HEK-293, but are not limited thereto.

In accordance with still another aspect of the present invention, there is provided a pharmaceutical composition for preventing or treating an angiogenesis-related disease, the pharmaceutical composition containing: (a) a pharmaceutically effective amount of the foregoing antibody against vegfr2 or antigen binding fragment thereof; and (b) a pharmaceutically acceptable carrier.

Since the pharmaceutical composition of the present invention uses, as an active ingredient, the Antibody against VEGFR2 or antigen binding fragment thereof of the present invention, the overlapping descriptions therebetween are omitted to avoid excessive complication of the specification due to repetitive descriptions thereof.

As used herein, the term "angiogenesis-related disease" refers to a disease caused by angiogenesis. Examples of the angiogenesis-related disease of the present invention include, but are not limited to, macular degeneration, diabetic retinopathy, cancer, psoriasis, rheumatoid arthritis, chronic inflammation, cancer, diabetic retinopathy, retinopathy of prematurity, corneal transplant rejection, neovascular glaucoma, hypochromia, proliferative retinopathy, hemophilic joints, capillary proliferation within atherosclerotic plaques, keloids, wound granulation, vascular adhesions, osteoarthritis, autoimmune diseases, Crohn's disease, restenosis, atherosclerosis, intestinal adhesions, cat scratch disease, ulcers, liver cirrhosis, glomerulonephritis, diabetic nephropathy, malignant nephrosclerosis, thrombotic microangiopathy, organ transplant rejection, glomerulopathy, diabetes, neurodegenerative diseases.

As validated in examples below, the antibody against VEGFR2 or antigen binding fragment thereof of the present invention inhibits the growth of vascular endothelial cells and inhibits angiogenesis and the invasion of vascular endothelial cells (FIGS. 3 and 4), and thus is effective in the prevention or treatment of angiogenesis-related diseases.

The pharmaceutically acceptable carrier contained in the pharmaceutical composition of the present invention is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further contain a lubricant, a wetting agent, a sweetening agent, a flavoring agent, an emulsifier, a suspending agent, a preservative, and the like, in addition to the above ingredients. Suitable pharmaceutically acceptable carriers and agents are described in detail in *Remington's Pharmaceutical Sciences* (19th ed., 1995).

The pharmaceutical composition of the present invention may be administered parenterally and may be administered through, for example, intravenous injection, subcutaneous injection, muscular injection, intraperitoneal injection, topical administration, intranasal administration, intrapulmonary administration, rectal administration, or the like.

The appropriate dose of the pharmaceutical composition of the present invention varies depending on factors, such as the formulating method, manner of administration manner, patient's age, body weight, gender, morbidity, and food, time of administration, route of administration, excretion rate, and response sensitivity. The ordinarily skilled practitioner can easily determine and prescribe the dose that is effective for the desired treatment or prevention. According to an embodiment of the present invention, the daily dose of the pharmaceutical composition of the present invention is 0.0001-100 mg/kg. As used herein, the term "pharmaceutically effective amount" refers to an amount sufficient to prevent or treat cancer.

The pharmaceutical composition of the present invention may be formulated into a unit dosage form or may be prepared in a multi-dose container by using a pharmaceutically acceptable carrier and/or excipient according to the method easily conducted by a person having an ordinary skill in the art to which the present invention pertains. Here, the dosage form may be a solution in an oily or aqueous medium, a suspension, an emulsion, an extract, a pulvis, a suppository, a powder, granules, a tablet, or a capsule, and may further include a dispersant or a stabilizer.

According to still another aspect of the present invention, the present invention provides a method for preventing or treating an angiogenesis-related disease, the method including a step for administering, to a subject, a pharmaceutical composition containing an antibody against VEGFR2 or an antigen binding fragment thereof as an active ingredient.

As used herein, the term "administration" or "administer" refers to the direct application of a therapeutically effective amount of the composition of the present invention to a subject (i.e., an object) in need of the composition, thereby forming the same amount thereof in the body of the subject.

The term "therapeutically effective amount" of the composition refers to the content of the composition, which is sufficient to provide a therapeutic or preventive effect to a subject to be administered, and thus the term has a meaning including "prophylactically effective amount." As used herein, the term "subject" comprises, but is not limited to, a human, mouse, rat, guinea pig, dog, cat, horse, cow, pig, monkey, chimpanzee, baboon, or rhesus monkey. Specifically, the subject of the present invention is a human.

Since the method for preventing or treating an angiogenesis-related disease of the present invention comprises the step of administering the pharmaceutical composition for preventing or treating an angiogenesis-related disease, which corresponds to an aspect of the present invention, the overlapping descriptions therebetween are omitted to avoid excessive complication of the specification.

The antibody of the present invention may be used in the diagnosis of, for example, an angiogenesis-related disease, disorder, or conditions.

Therefore, In accordance with another aspect of the present invention, there is provided a kit for diagnosing an angiogenesis-related disease, disorder, or conditions, the kit comprising the foregoing antibody of the present invention.

Since the diagnostic kit of the present invention comprises an antibody against VEGFR2 or antigen binding fragment thereof of the present invention, and is used to diagnose the same disease as the pharmaceutical composition of the present invention, the overlapping descriptions therebetween are omitted to avoid excessive complication of the specification due to repetitive descriptions thereof.

In addition, the antibody of the present invention may be used to analyze whether there is drug responsiveness to the antibody of the present invention in a patient.

Therefore, according to another embodiment of the present invention, the present invention provides a drug responsiveness analysis kit containing the foregoing antibody of the present invention.

The analysis kit of the present invention may be used to analyze whether there is drug responsiveness to the antibody of the invention in a particular patient. For example, if the antibody of the present invention shows a binding result when the cells of a patient are treated with the antibody of the present invention, it can be determined that there is drug responsiveness to the antibody of the present invention in that patient.

The foregoing kit contains antibodies, and thus can be manufactured suitable for various immunoassay or immunostaining methods. The immunoassay or immunostaining methods include, but are not limited to, radioactive immunoassay, radioactive immunoprecipitation, immunoprecipitation, enzyme-linked immunosorbent assay (ELISA), capture-ELISA, inhibition or competition analysis, sandwich assay, flow cytometry, immunofluorescence, and immunoaffinity purification. The immunoassay or immunostaining methods are disclosed in *Enzyme Immunoassay*, E. T. Maggio, ed., CRC Press, Boca Raton, Fla., 1980; Gaastra, W., *Enzyme-linked immunosorbent assay (ELISA)*, in *Methods in Molecular Biology*, Vol. 1, Walker, J. M. ed., Humana Press, N J, 1984; and Ed Harlow and David Lane, *Using Antibodies: A Laboratory Manual*, Cold Spring Harbor Laboratory Press, 1999, the contents of which are incorporated herein by reference.

For example, when the method of the present invention is performed according to the radioimmunoassay method, antibodies labeled with a radioactive isotope (e.g., $C^{14}$, $I^{125}$, $P^{32}$, and $S^{35}$) may be used to detect receptors on the surface of vascular endothelial cells surrounding cancer cells. When the method of the present invention is performed according to the ELISA method, a particular embodiment of the present invention comprises the steps of: (i) coating a surface of a solid substrate with a sample to be analyzed; (ii) incubating antibody against VEGFR2 as primary antibody and the cell lysate; (iii) incubating the product in step (ii) and a secondary antibody conjugated to an enzyme; and (iv) determining the activity of the enzyme.

A suitable example of the solid substrate is a hydrocarbon polymer (e.g., polystyrene and polypropylene), glass, a metal, or a gel, and most preferably a microtiter plate.

The enzyme conjugated to the secondary antibody comprises, but is not limited to, enzymes that catalyze a colorimetric reaction, a fluorescent reaction, a luminescent reaction, or an infrared reaction, and comprises for examples alkaline phosphatase, β-galactosidase, horseradish peroxidase, luciferase, and cytochrome $P_{450}$. In cases where alkaline phosphatase is used as an enzyme conjugated to the secondary primary, colorimetric reaction substrates may be used such as bromo-chloro-indolyl phosphate (BCIP), nitroblue tetrazolium (NBT), naphthol-AS-B1-phosphate, and enhanced chemifluorescence (ECF); and in cases where horseradish peroxidase is used as an enzyme conjugated to the secondary primary, substrates may be used, such as chloronaphthol, aminoethyl carbazole, diaminobenzidine, D-luciferin, lucigenin (bis-N-methylacridinium nitrate), resorufin benzyl ether, luminol, 10-acetyl-3,7-dihydroxyphenoxazine (Amplex Red reagent), p-phenylenediamine-HCl and pyrocatechol (HYR), tetramethylbenzidine (TMB), 2,2'-Azine-di[3-ethylbenzthiazoline sulfonate] (ABTS), o-phenylenediamine (OPD), and naphthol/pyror, glucose oxidase, t-NBT (nitroblue tetrazolium) and m-PMS (phenazine methosulfate).

In cases where the method of the present invention is performed by capture-ELISA, a particular embodiment of the present invention comprises the steps of: (i) coating a surface of a solid substrate with antibody against VEGFR2 as a capturing antibody; (ii) reacting the capturing antibody with a sample; (iii) reacting the product in step (ii) with a VEGFR2 detecting antibody conjugated to a label generating a signal; and (iv) measuring the signal generated from the label.

The detecting antibody has a label that generates a detectable signal. Examples of the label include, but are not limited to, chemicals (e.g., biotin), enzymes (alkaline phosphatase, β-galactosidase, horseradish peroxidase, and cytochrome P450), radioactive substances (e.g., $C^{14}$, $I^{125}$, $P^{32}$, and $S^{35}$), fluorescent substances (e.g., fluorescein), light-emitting substances, chemiluminescent substances, and fluorescence resonance energy transfer (FRET). Various labels and labeling methods are described in Ed Harlow and David Lane, Using Antibodies: A Laboratory Manual, Cold Spring Harbor Laboratory Press, 1999.

In the ELISA method or capture-ELISA method, the measurement of the funeral enzyme activity or the measurement of signals may be carried out according to various methods known in the art. A signal may be easily detected using streptavidin when biotin is used as a label, and a signal may be easily detected using luciferin when luciferase is used as a label.

Examples of the sample application to the kit of the present invention include, but are not limited to, cells, tissues or tissue-derived extracts, lysate or purified materials, blood, plasma, serum, lymph, or ascites.

The antibody of the present invention may be used in in vivo or in vitro imaging. According to another aspect of the present invention, the present invention provides a composition for imaging, containing a conjugate in which the antibody of the present invention is conjugated to a label generating a detectable signal conjugated to the antibody.

Examples of the label capable of generating a detectable signal include, but are not limited to, T1 contrast materials (e.g., Gd chelate compounds), T2 contrast materials (e.g., superparamagnetic materials (e.g., magnetite, $Fe_3O_4$, γ-$Fe_2O_3$, manganese ferrite, cobalt ferrite, and nickel ferrite)), radioactive isotopes (e.g., $^{11}C$, $^{15}O$, $^{13}N$, $P^{32}$, $S^{35}$, $^{44}Sc$, $^{45}Ti$, $^{118}I$, $^{136}La$, $^{198}Tl$, $^{200}Tl$, $^{205}Bi$, and $^{206}Bi$), fluorescent materials (fluorescein, phycoerythrin, rhodamine, lissamine, and Cy3/Cy5), chemiluminescent materials, magnetic particles, mass labels, and dense electron particles.

The antibody of the present invention can be used alone to treat angiogenesis-related diseases, but can target VEGFR2-expressing cells, and thus the antibody of the present invention can be provided in the form of an antibody drug conjugate (ADC) by binding to other drugs.

According to another aspect of the present invention, the present invention provides an antibody drug conjugate (ADC) containing the antibody of the present invention and a drug conjugated to the antibody.

A drug conjugated to the antibody of the present invention is not particularly limited, and comprises chemical substances, radionuclides, immunotherapeutic agents, cytokines, chemokines, toxins, biological agents, and enzyme inhibitors, and more specifically, the following anticancer drugs: acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol, beta-2-deoxythioguanosine, bisantrene HCl, bleomycin sulfate, busulfan, buthionine sulfoximine, BWA773U82, BW502U83/HCl, BW7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydro galactitol, diaziquone, dibromodulcitol, didemnin B, diethyldithiocarbamate, diglycoaldehyde, dihydro-5-azacytine, doxorubicin, echinomycin, dedatrexate, edelfosine, eplolnitin, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5'-fluorouracil, Fluosol™, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, 4-ipomeanole, iproplatin, isotretinoin, leucovorin calcium, leuprolide acetate, levamisole, liposome daunorubicin, liposome encapsulated doxorubicin, lomustine, lonidamine, maytansine, mechlorethamine hydrochloride, melphalan, menogaril, merbarone, 6-mercaptopurine, mesna, methanol extract of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor (TNF), uracil mustard, vinblastine sulfate, vincristine sulfate, vindesine, vinorelbine, vinzolidine, Yoshi 864, zorubicin, cytosine arabinoside, etoposide, melphalan, taxotele, and taxol.

Advantageous Effects

Features and advantages of the present invention are summarized as follows.

(a) The present invention is directed to: an antibody against vegfr2 or an antigen binding fragment thereof, the antibody containing novel sequence type heavy chain and light chain CDR amino acid sequences; nucleic acid molecules encoding heavy chain and light chain variable regions of the antibody against vegfr2 and containing novel amino acid sequences; recombinant vectors containing the nucleic acid molecules of the present invention; host cells transformed with the recombinant vectors of the present invention; a pharmaceutical composition containing the antibody or antigen binding fragment thereof of the present invention for preventing or treating an angiogenesis-related disease; a method for preventing or treating an angiogenesis-related disease; a diagnostic kit; and a kit for analysis of drug responsiveness.

(b) The antibody of the present invention is an antibody that specifically binds to VEGFR2 overexpressed in vascular endothelial cells and an antibody that binds to a different epitope compared with ramucirumab. In addition, the antibody of the present invention has very low homology compared with CDR sequences of conventional VEGFR2-targeting antibodies, and thus has distinctive sequences.

(c) The antibody of the present invention has equivalent activity to ramucirumab, and has activity to inhibit the growth of angiogenesis-related cells, inhibit angiogenesis, and inhibit the invasion of vascular endothelial cells, and thus the antibody of the present invention is very effective in the prevention or treatment of an angiogenesis-related disease.

(d) The activity of the antibody of the present invention to inhibit the growth of vascular endothelial cells can be used to prevent or treat an angiogenesis-related disease.

(e) The antibody of the present invention can be used as not only a therapeutic agent for an angiogenesis-related disease but also drug responsiveness analysis, imaging, and an antibody drug conjugate (ADC).

BRIEF DESCRIPTION OF THE DRAWINGS

FIG. 2A shows the ability of 1A10 antibody to inhibit the VEGF-VEGFR2 binding by binding with VEGFR2, and FIG. 2B shows the ability of 1A10 antibody to inhibit the previously formed VEGF-VEGFR2 binding. RAMU (ramucirumab) and hIgG (human IgG) were used as a positive control and a negative control, respectively.

MODE FOR CARRYING OUT THE INVENTION

Figure 1:
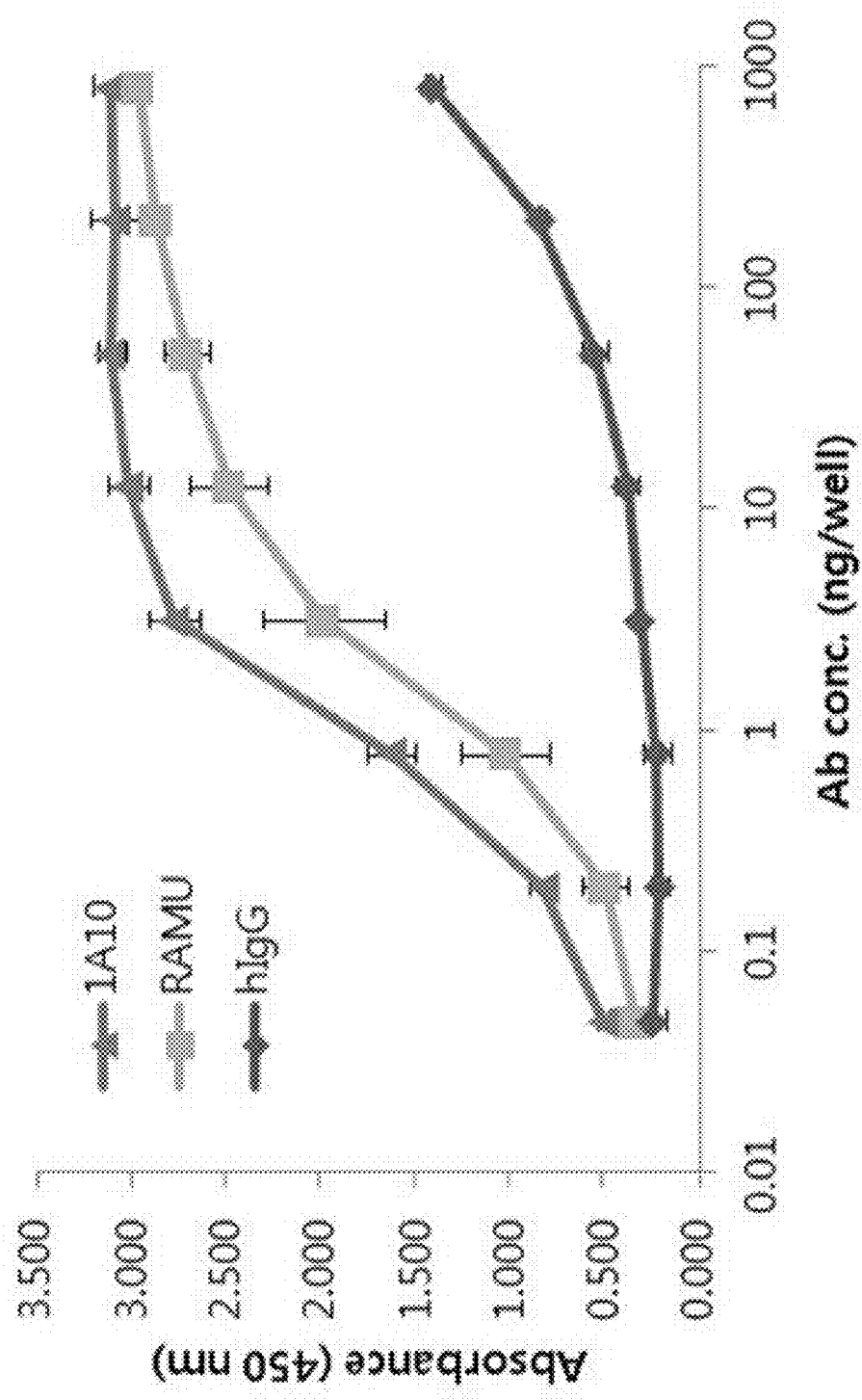
FIG. 1 is a graph showing the binding ability of 1A10 antibody to human VEGFR2. RAMU (ramucirumab) and hIgG (human IgG) were used as a positive control and a negative control, respectively.

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1: Development of Antibody Against Vegfr2

For antibody development, the extracellular domain (ECD) of VEGFR2 protein was produced using animal cells, and then used as an antigen. The DNA having a form in which hinge and Fc regions ($CH_2$—$CH_3$) of human IgG1 were bound to the C-terminus of ECD was cloned into pCEP4 vector (Invitrogen, Cat. No. V044-50). Then, the cloned vector was transiently transformed into the FreeStyle™ 293F (Invitrogen, Cat. No. R790-07) cells to obtain the VEGFR2-ECD Fc fusion protein. Phage bio-panning was performed using the VEGFE2-ECD Fc fusion protein and the OPAL library. The antibody library was obtained in a phage form using a VCSM13 helper phage, and used for panning. The number of library phages binding to primary antigen was $10^{12}$. The panning round was performed up to 4 rounds. A method in which the amount of antigen is decreased and the number of times of washing is increased as the number of panning rounds increases was employed as a panning strategy in which selective phages with high affinity can be selectively selected. The number of phages binding to the target antigen was titrated as follows by using ER2537 E. coli. The binder phages obtained in each round of bio-panning were eluted with a glycine buffer of pH 2.5. The ER2537 cells incubated in SB medium overnight were sub-cultured with a dilution of 1/200 using fresh SB medium. Then, the cells were further incubated at 37° C. for 3 hours to reach log phase. Then, 100 µl of fresh ER2537 and 10 µl of diluted phages were mixed in a 1.5 µl tube, incubated for 30 minutes, and plated on ampicillin LB plates. After incubation at 37° C. overnight, the number of phages was measured by applying the number of generated colonies and the dilution factor. The binder phages obtained in each round of bio-panning were infected in ER2537, and while the form of colonies was maintained, the binding to each antigen was examined by ELISA. The colonies obtained by infecting the binder phages were inoculated into the SB culture medium, and then incubated until the $OD_{600}$ value reached 0.5. Then, 0.5 mM IPTG was added thereto, followed by shaking at 30° C., thereby allowing Fab protein to be overexpressed. Fab proteins were purified using TES buffer. Purified Fab proteins were treated on the plates coated with VEGFR2-ECD Fc protein. After treatment with secondary antibody, a colorimetric reaction was induced using Absignal (AbClon, cat. #. AbC3001), and the $OD_{450}$ value was measured using an ELISA reader (Victor X3 PerkinElmer). As for antibody clones selected as specifically binding to VEGFR2, the nucleotide sequences of variable regions were examined through sequencing analysis using a phagemid plasmid and a known primer set (Phage display: a laboratory manual, Carlos Barbas III, et al., Cold Spring Harbor Laboratory Press). The 1A10 having excellent binding ability to VEGFR2 was selected from the selected antibodies and subjected to IgG conversion. The nucleotide sequences of variable regions of the selected 1A10 antibody are shown in Table 1.

TABLE 1

Amino acid sequences of the complementarity determining regions (CDRs) of 1A10 antibody

|  | Light chain | Heavy chain |
| --- | --- | --- |
| CDR1 | TGSSSNIGNYYVY (SEQ ID NO: 4) | DYDMS (SEQ ID NO: 1) |
| CDR2 | ANSHRPS (SEQ ID NO: 5) | SIYPGDSSTYYADSVKG (SEQ ID NO: 2) |
| CDR3 | ATWDASLSGYV (SEQ ID NO: 6) | EEVAFDY (SEQ ID NO: 3) |

Example 2: Verification of Effect of 1A10 Antibody on VEGF-VEGFR2 Binding

It was examined using ELISA whether the IgG-converted 1A10 antibody binds to VEGFR2. The binding to VEGFR2 was examined at eight concentrations obtained by sequential dilution of 1:4 from a maximum of 800 ng/well (FIG. 1).

Figure 2A:
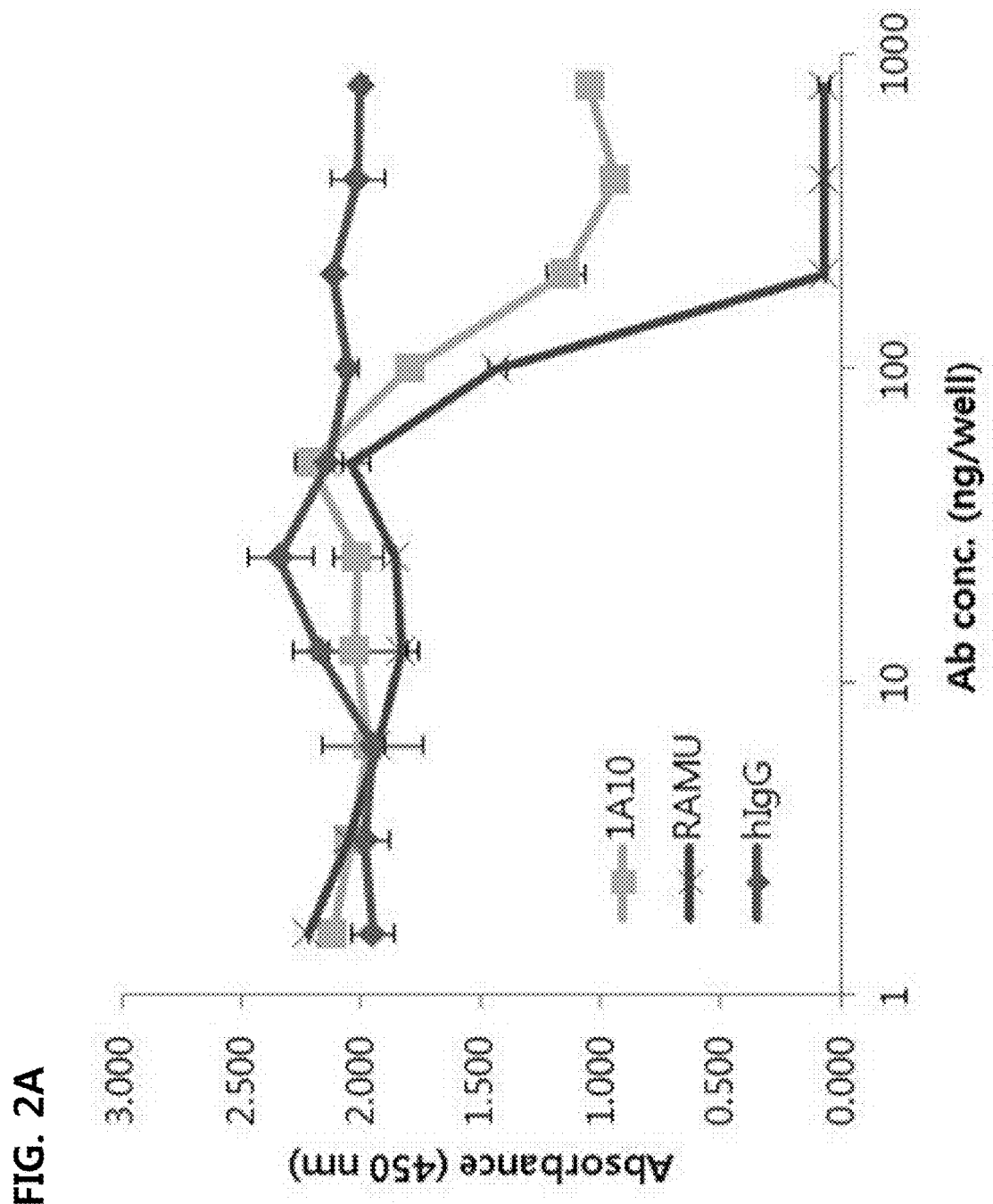
FIGS. 2A and 2B are graphs showing the ability of 1A10 antibody to inhibit VEGF-VEGFR2 binding.

The effect of the 1A10 antibody on the VEGF-VEGFR2 binding was examined by ELISA. After VEGF was coated on a 96-well plate, VEGFR2 and antibodies were mixed, followed by incubation for 1 hour. For the detection of antibodies binding to VEGF, an anti-human IgG-Fc secondary antibody was incubated, and then color developed using TMB (FIG. 2A).

Figure 2B:
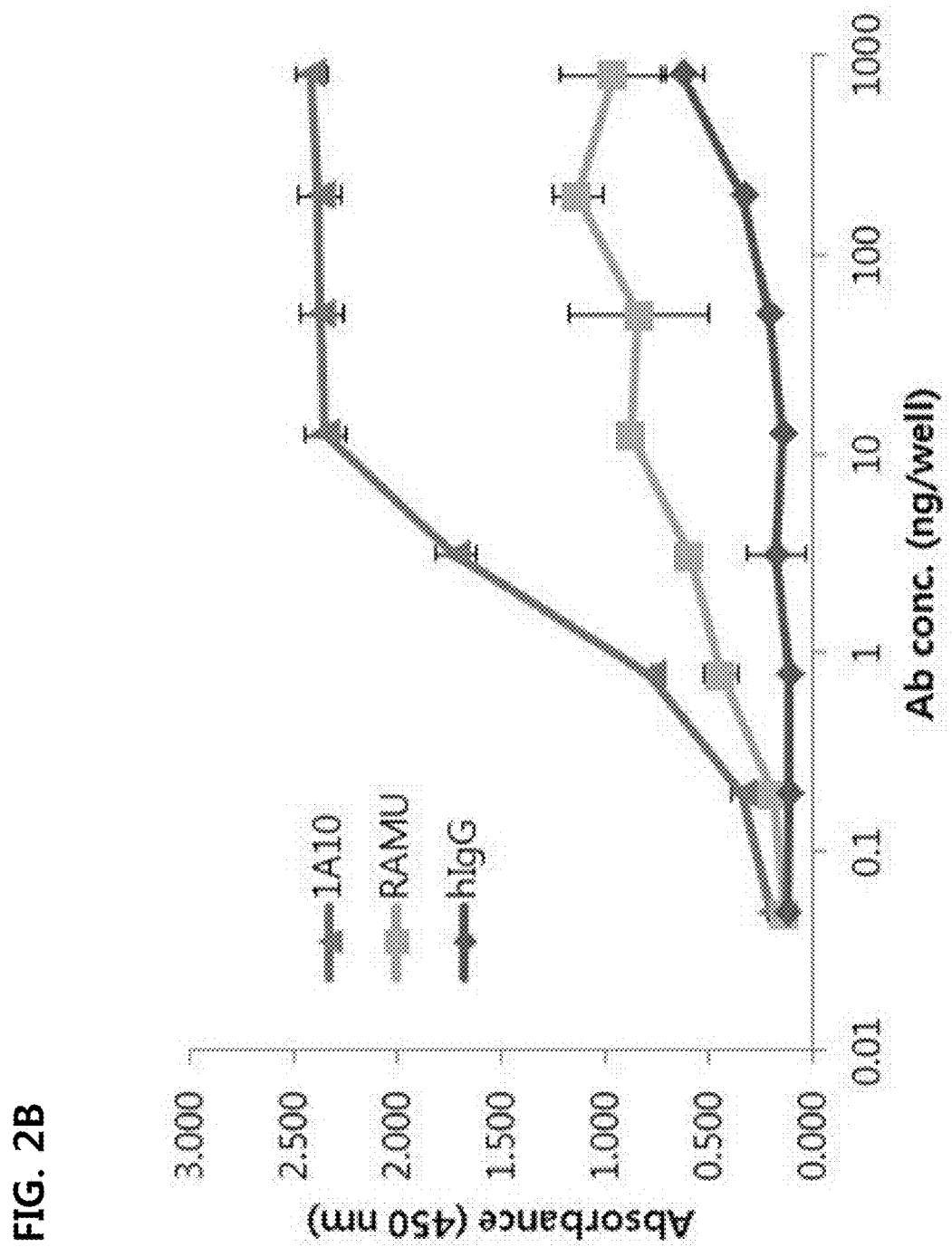

It was examined using ELISA whether the previously formed VEGF-VEGFR2 binding can be regulated by the 1A10 antibody. VEGF was coated on a 96-well plate. and then VEGFR2 was previously incubated with coated VEGF. After the antibodies were incubated in the well having VEGFVEGFR2 complex formed thereon, unbound antibodies were washed with PBS. The bound antibodies were incubated with the anti-human IgG-Fab secondary antibody, and then color-developed using TMB (FIG. 2B).

The results confirmed that the 1A10 antibody bound to VEGFR2 to inhibit the binding of VEGF and VEGFR2 and also inhibited the previously formed VEGF-VEGFR2 binding.

Figure 3A:
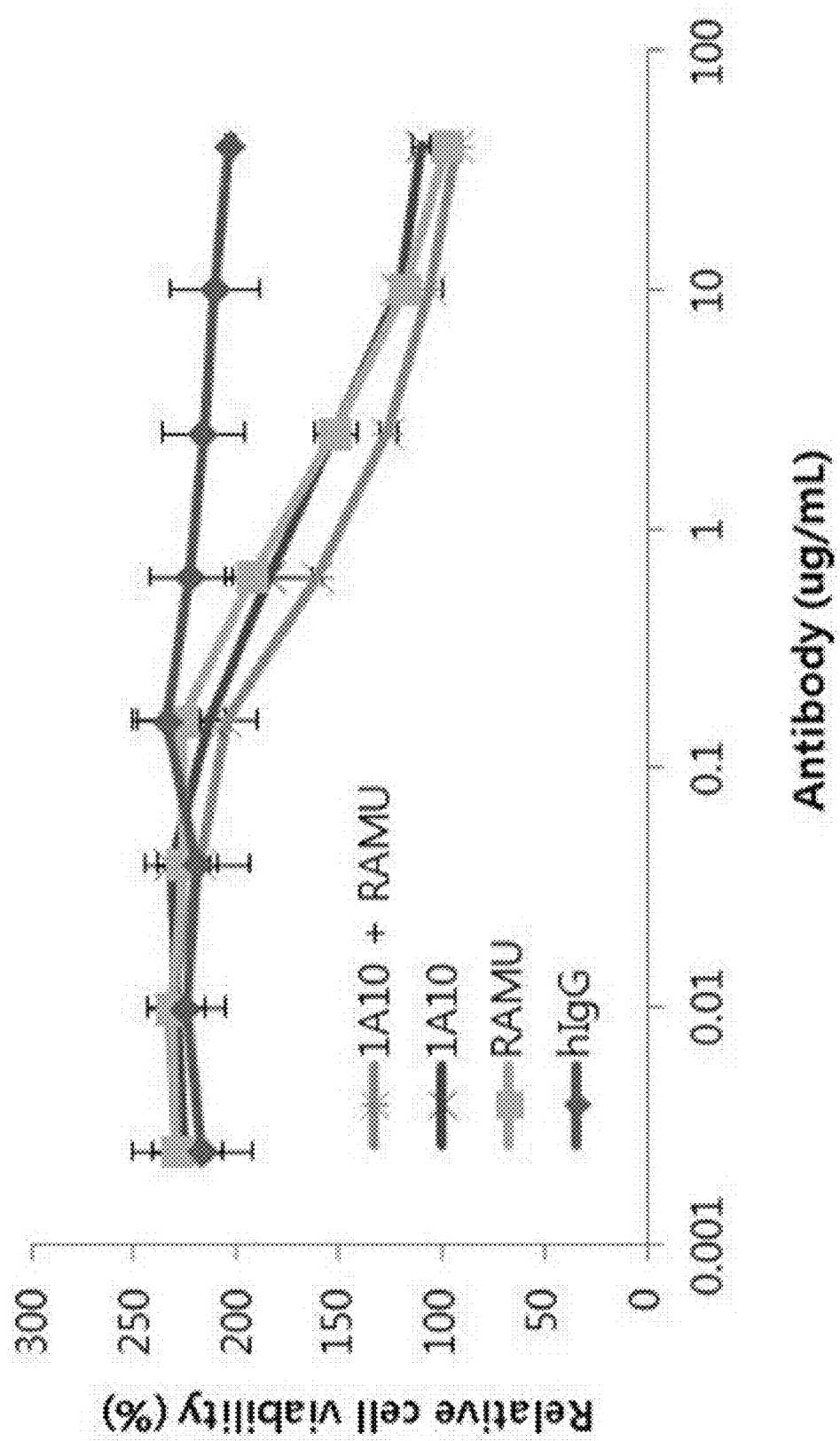
FIGS. 3A and 3B are graphs showing the proliferation inhibitory ability by treatment of vascular endothelial cells HUVEC with 1A10 antibody alone and with 1A10 antibody and ramucirumab in combination. Experiments were conducted with the induction of cell growth by VEGF in FIG. 3A and without the induction of cell growth by VEGF in FIG. 3B. RAMU (ramucirumab) and hIgG (human IgG) were used as a positive control and a negative control, respectively.
Figure 3B:
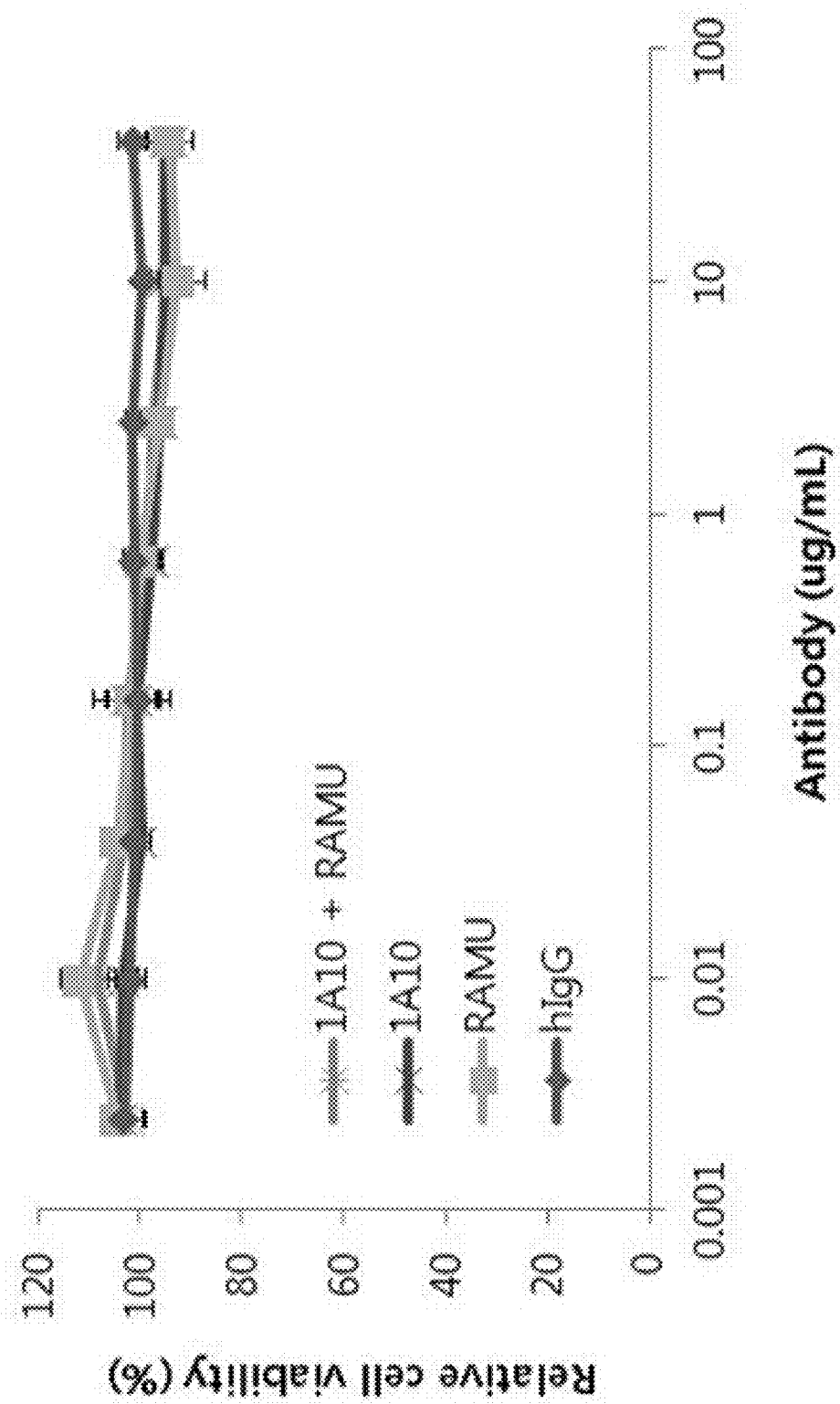

Example 3: Comparison of Vascular Endothelial Cell Growth Inhibitory Effect of 1A10 Antibody For the examination of the vascular endothelial cell proliferation inhibitory effect, cell viability analysis was conducted. The cell viability analysis was performed on representative VEGFR2-overexpressing human vascular endothelial cells (HUVECs), which were treated with 1A10 antibody alone or in combination with ramucirumab. For the combinative treatment, 1A10 antibody and ramucirumab were mixed at a ratio (weight ratio) of 1:1. HUVEC (Lonza, Cat No. CC-2519, 3,500 cells/well) cells were dispensed in a 96-well plate, and incubated for 24 hours. For the examination of cell growth induced by VEGF, the cells were incubated in 1% FBS for 6 hours, and the purified antibodies were serially diluted 1:4 starting from a maximum of 40 µg/ml, and then used for the treatment at 8 concentrations. After the treatment for 1 hour, VEGF treatment was conducted until the final concentration was 50 ng/ml, and after 27 hours, cell viability analysis was performed. As shown in FIG. 3A, it was confirmed that, at the time of treatment with single antibody, the 1A10 antibody inhibited the growth of vascular endothelial cells at a level equivalent to that of ramucirumab. However, it could not be confirmed that, at the time of co-treatment with the 1A10 antibody and ramucirumab, the growth inhibitory activity was significantly increased. In addition, it was confirmed that both 1A10 antibody and ramucirumab antibody did not inhibit the growth inhibition of vascular endothelial cells incubated in normal medium without the induction of VEGF (FIG. 3A).

Figure 4A:
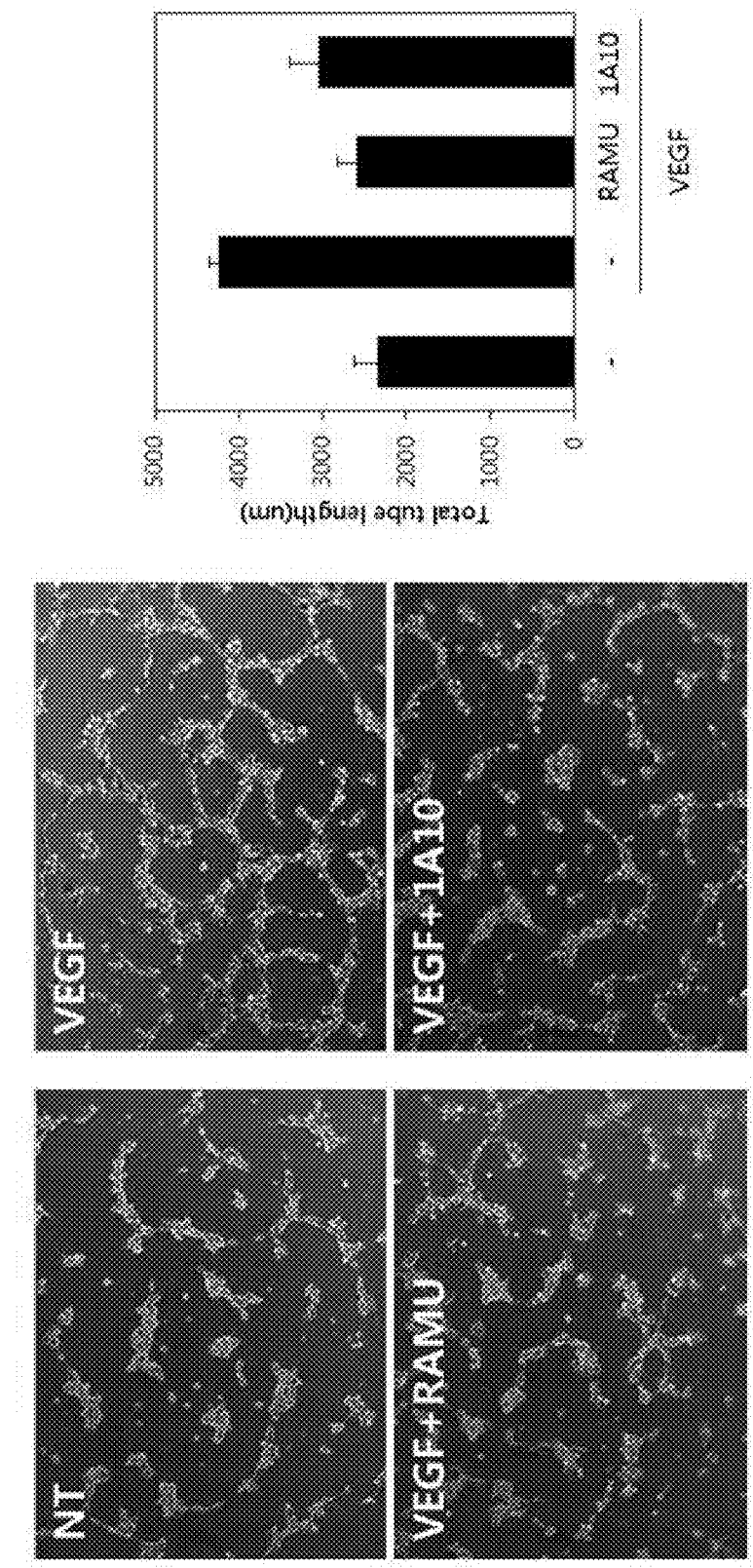
FIGS. 4A and 4B show the ability of 1A10 antibody to inhibit tube formation and invasion of vascular 20 endothelial cell.

Example 4: Effect of 1A10 Antibody on Tube Formation and Invasion of Vascular Endothelial Cells The new blood vessels can be formed only when a vascular shape of capillary formation occurs by the migration of vascular endothelial cells. Therefore, the effect of 1A10 antibody on the capillary formation of endothelial cells was examined. The 48-well plate was coated with 150 µl of Matrigel, followed by polymerization at 37° C. for 2 hours. HUVECs were inoculated into Matrigel, and the antibody was added thereto, and then 50 ng/ml of VEGF was added. The cell morphological changes were observed under a microscope, and analyzed using the ImageJ Angiogenesis Analyzer (FIG. 4A).

Figure 4B:
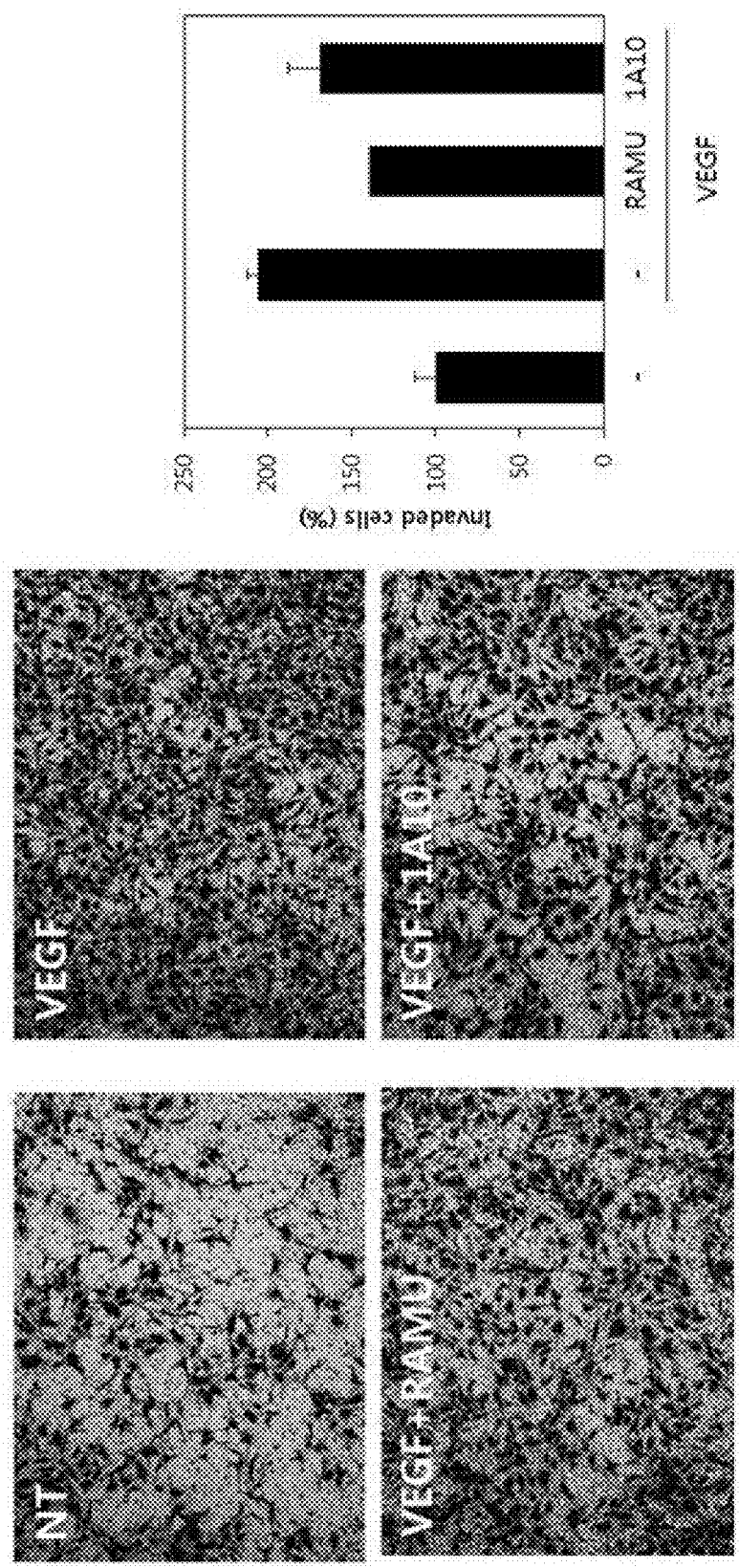

One of the other characteristics of vascular endothelial cells is the destruction and penetration of their own basement membranes by migration of endothelial cells. Therefore, the effect of the 1A10 antibody on the invasion of endothelial cells was examined. The invasion of HUVECs was carried out in vitro using a trans-well chamber system with a polycarbonate filter. A lower portion of the filter was coated with gelatin, and an upper portion of the filter was coated with Matrigel. After the addition of 50 ng/ml of VEGF and 1A10 antibody to a lower well containing 600 µl of the culture, a chamber was placed therein, and then HUVECs were added into the upper portion, followed by treatment at a constant temperature for 20 hours. The cells were fixed with 70% methanol, stained with hematoxylin/eosin, and then, the whole cells in one filter were quantified under a microscope to determine the degree of cell invasion (FIG. 4B).

The above results confirmed that the 1A10 antibody inhibited angiogenesis by inhibiting tube formation and invasion of HUVECs, which are main characteristics of angiogenesis of HUVECs.

Example 5: VEGFR2 Cell Signaling Inhibitory Effect of 1A10 Antibody

For the analysis of the mechanism of growth inhibitory effect of 1A10 antibody on VEGFR2-overexpressing vascular endothelial cells, the intracellular signaling system inhibitory effect of VEGFR2 was analyzed. 10 µg/ml of 1A10 antibody was added to HUVEC cells incubated in serum-free medium for 6 hours, followed by incubation for 1 hour. Then, after the signaling system was activated with 50 ng/ml of VEGF for 10 minutes, a cell extraction liquid (50 mM Tris, pH 7.4, 150 mM NaCl, 1% NP-40, 0.1% sodium dodecyl sulfate, 1 mM NaF, 1 mM Na3VO4, 1 mM PMSF, and protease inhibitor cocktail (Sigma)) was added thereto to obtain cell extracts. Thereafter, proteins of the cell extracts were analyzed by the Western blot method. For the analysis, pVEGFR2 (#4991), VEGFR2 (#2472), ERK (#4695), and pERK (#4370) antibody (Cell Signaling Technology) were used. Actin (AbClon, # Abc-2002) was used as a loading control. Each protein was analyzed using HRP-conjugated anti-rabbit antibody (Pierce, #31463) and Absignal (AbClon, # AbC-3001) reagent.

Figure 5:
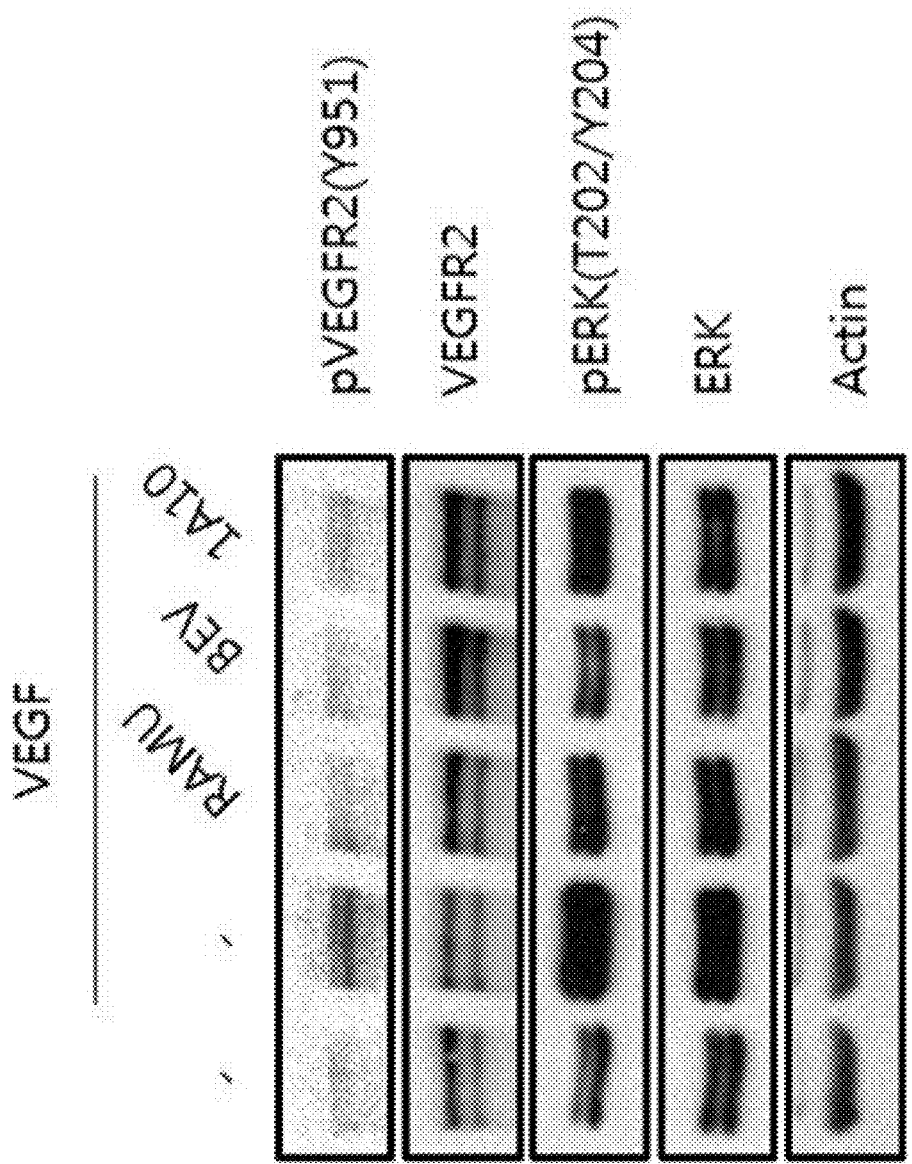
FIG. 5 shows the ability of 1a10 antibody to inhibit VEGFR2 cell signaling. The decrease in VEGFR2 downstream signaling by 1A10 antibody, ramucirumab, and bevacizumab were examined using western blot.

As shown in FIG. 5, it was confirmed that p (phosphorylated)-VEGFR2 and p-ERK protein decreased when treated with 1A10 antibody alone.

The results showed that the treatment with 1A10 antibody alone controlled the phosphorylation of VEGFR2 in a manner equivalent to that of ramucirumab, thereby inhibiting downstream signaling systems. Especially, it could be confirmed that the 1A10 antibody affected the phosphorylation of ERK involved in cell growth.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. An antibody against vascular endothelial growth factor receptor 2 (VEGFR2) or an antigen binding fragment thereof, the antibody or antigen binding fragment thereof comprising:
   (a) a heavy chain variable region comprising the following heavy chain complementarity determining region (CDR) amino acid sequences: CDRH1 of SEQ ID NO: 1, CDRH2 of SEQ ID NO: 2, and CDRH3 of SEQ ID NO: 3; and
   (b) a light chain variable region comprising the following light chain CDR amino acid sequences: CDRL1 of SEQ ID NO: 4, CDRL2 of SEQ ID NO: 5, and CDRL3 of SEQ ID NO: 6.

2. The antibody or antigen binding fragment thereof of claim 1, wherein the heavy chain variable region comprises the amino acid sequence of SEQ ID NO: 8.

3. The antibody or antigen binding fragment thereof of claim 1, wherein the light chain variable region comprises the amino acid sequence of SEQ ID NO: 10.

4. A pharmaceutical composition for preventing or treating an angiogenesis-related disease, the pharmaceutical composition comprising: (a) a pharmaceutically effective amount of the antibody against VEGFR2 or antigen binding fragment thereof of claim 1; and (b) a pharmaceutically acceptable carrier.

5. The pharmaceutical composition of claim 4, wherein the angiogenesis-related disease is selected from the group consisting of macular degeneration, diabetic retinopathy, cancer, psoriasis, rheumatoid arthritis, chronic inflammation, cancer, diabetic retinopathy, retinopathy of prematurity, corneal transplant rejection, neovascular glaucoma, hypochromia, proliferative retinopathy, hemophilic joints, capillary proliferation within atherosclerotic plaques, keloids, wound granulation, vascular adhesions, osteoarthritis, autoimmune diseases, Crohn's disease, restenosis, atherosclerosis, intestinal adhesions, cat scratch disease, ulcers, liver cirrhosis, glomerulonephritis, diabetic nephropathy, malignant nephrosclerosis, thrombotic microangiopathy, organ transplant rejection, glomerulopathy, diabetes, and neurodegenerative diseases.

6. A nucleic acid molecule encoding a heavy chain variable region of an antibody against VEGFR2, the heavy chain variable region comprising the amino acid sequence of SEQ ID NO: 8.

7. A recombinant vector comprising the nucleic acid molecule of claim 6.

8. A host cell transformed with the recombinant vector of claim 7.

9. The nucleic acid molecule of claim 6, wherein the nucleic acid molecule comprises the nucleotide sequence of SEQ ID NO: 7.

10. A recombinant vector comprising the nucleic acid molecule of claim 9.

11. A host cell transformed with the recombinant vector of claim 10.

12. A nucleic acid molecule encoding a light chain variable region of an antibody against VEGFR2, the light chain variable region comprising the amino acid sequence of SEQ ID NO: 10.

13. A recombinant vector comprising the nucleic acid molecule of claim 12.

14. A host cell transformed with the recombinant vector of claim 13.

15. The nucleic acid molecule of claim 12, wherein the nucleic acid molecule comprises the nucleotide sequence of SEQ ID NO: 9.

16. A recombinant vector comprising the nucleic acid molecule of claim 15.

17. A host cell transformed with the recombinant vector of claim 16.

18. A kit for diagnosis of an angiogenesis-related disease or analysis of drug responsiveness, the kit comprising the antibody against VEGFR2 or antigen binding fragment thereof of claim 1.

19. A method for treating an angiogenesis-related disease, the method comprising a step for administering to a subject a pharmaceutical composition comprising, as an active ingredient, the antibody against VEGFR2 or antigen binding fragment thereof of claim 1.

* * * * *

SEQUENCE LISTING

<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: CDRH1 of 1A10 antibody

<400> SEQUENCE: 1

Asp Tyr Asp Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: CDRH2 of 1A10 antibody

<400> SEQUENCE: 2

Ser Ile Tyr Pro Gly Asp Ser Ser Thr Tyr Tyr Ala Asp Ser Val Lys
1               5                   10                  15

Gly

<210> SEQ ID NO 3
<211> LENGTH: 7
<212> TYPE: PRT
<213> ORGANISM: Artificial Sequence
<220> FEATURE:
<223> OTHER INFORMATION: CDRH3 of 1A10 antibody

<400> SEQUENCE: 3

Glu Glu Val Ala Phe Asp Tyr
1               5

<210> SEQ ID NO 4
<211> LENGTH: 13
<212> TYPE: PRT
<213> ORGANISM: Artificial Sequence
<220> FEATURE:
<223> OTHER INFORMATION: CDRL1 of 1A10 antibody

<400> SEQUENCE: 4

Thr Gly Ser Ser Ser Asn Ile Gly Asn Tyr Tyr Val Tyr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDRL2 of 1A10 antibody

<400> SEQUENCE: 5

Ala Asn Ser His Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: CDRL3 of 1A10 antibody

<400> SEQUENCE: 6

Ala Thr Trp Asp Ala Ser Leu Ser Gly Tyr Val
1               5                   10

<210> SEQ ID NO 7
<211> LENGTH: 348
<212> TYPE: DNA
<213> ORGANISM: Artificial Sequence
<220> FEATURE:
<223> OTHER INFORMATION: Nucleotide sequence of 1A10 heavy chain
      variable region

<400> SEQUENCE: 7

```
gaggtgcagc tgttggagtc tgggggaggc ttggtacagc ctgggggtc cctgagactc        60 tcctgtgcag cctctggatt caccttttagc gattatgata tgagctgggt ccgccaggct      120
ccagggaagg gctggagtg gtctcatcg atctatcctg gtgatagtag tacatattac        180
gctgattctg taaaaggtcg gttcaccatc tccagagaca attccaagaa cacgctgtat      240
ctgcaaatga acagcctgag agccgaggac acggccgtgt attactgtgc gaaagaggag      300
gtggctttcg actactgggg ccagggtaca ctggtcaccg tgagctca                   348
```

<210> SEQ ID NO 8
<211> LENGTH: 116
<212> TYPE: PRT
<213> ORGANISM: Artificial Sequence
<220> FEATURE:
<223> OTHER INFORMATION: Amino acid sequence of 1A10 heavy chain
      variable region

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Ser Ile Tyr Pro Gly Asp Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Glu Val Ala Phe Asp Tyr Trp Gly Gln Gly Thr Leu Val
            100                 105                 110

Thr Val Ser Ser
        115

<210> SEQ ID NO 9
<211> LENGTH: 330
<212> TYPE: DNA
<213> ORGANISM: Artificial Sequence
<220> FEATURE:
<223> OTHER INFORMATION: Nucleotide sequence of 1A10 light chain
      variable region

<400> SEQUENCE: 9

```
cagtctgtgc tgactcagcc accctcagcg tctgggaccc ccgggcagag ggtcaccatc       60
tcttgtactg gctcttcatc taatattggc aattattatg tctactggta ccagcagctc      120
ccaggaacgg cccccaaact cctcatctat gctaatagtc atcggccaag cggggtccct      180
gaccgattct ctggctccaa gtctggcacc tcagcctccc tggccatcag tgggctccgg      240
```

```
tccgaggatg aggctgatta ttactgtgct acttgggatg ctagcctgag tggttatgtc    300
ttcggcggag gcaccaagct gacggtccta                                     330
```

<210> SEQ ID NO 10
<211> LENGTH: 110
<212> TYPE: PRT
<213> ORGANISM: Artificial Sequence
<220> FEATURE:
<223> OTHER INFORMATION: Amino acid sequence of 1A10 light chain variable region

<400> SEQUENCE: 10

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Tyr
            20                  25                  30

Tyr Val Tyr Trp Tyr Gln Gln Leu Pro Gly Thr Ala Pro Lys Leu Leu
        35                  40                  45

Ile Tyr Ala Asn Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Ala Ser Leu
                85                  90                  95

Ser Gly Tyr Val Phe Gly Gly Gly Thr Lys Leu Thr Val Leu
            100                 105                 110
```

<210> SEQ ID NO 11
<211> LENGTH: 324
<212> TYPE: DNA
<213> ORGANISM: Artificial Sequence
<220> FEATURE:
<223> OTHER INFORMATION: Constant region of human IgG kappa chain

<400> SEQUENCE: 11

```
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagttcgcc cgtcacaaag   300
agcttcaaca ggggagagtg ttaa                                          324
```

<210> SEQ ID NO 12
<211> LENGTH: 107
<212> TYPE: PRT
<213> ORGANISM: Artificial Sequence
<220> FEATURE:
<223> OTHER INFORMATION: Constant region of human IgG kappa chain

<400> SEQUENCE: 12

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
```

```
              50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 13
<211> LENGTH: 993
<212> TYPE: DNA
<213> ORGANISM: Artificial Sequence
<220> FEATURE:
<223> OTHER INFORMATION: Constant region of human IgG heavy chain

<400> SEQUENCE: 13

```
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgcg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc cccgggtaaa tga                                   993
```

<210> SEQ ID NO 14
<211> LENGTH: 330
<212> TYPE: PRT
<213> ORGANISM: Artificial Sequence
<220> FEATURE:
<223> OTHER INFORMATION: Constant region of human IgG heavy chain

<400> SEQUENCE: 14

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80
```

-continued

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```